(12) United States Patent
Derrieu

(10) Patent No.: US 9,107,812 B2
(45) Date of Patent: Aug. 18, 2015

(54) PHARMACEUTICAL COMPOSITION CONTAINING AN N-PHENYLPYRAZOLE DERIVATIVE AND GLYCOFUROL, USE FOR THE PREPARATION OF A TOPICAL VETERINARY MEDICAMENT FOR COMBATING FLEAS

(75) Inventor: Guy Derrieu, Cagnes sur Mer (FR)

(73) Assignee: VIRBAC, Carros (FR)

( * ) Notice: Subject to any disclaimer, the term of this patent is extended or adjusted under 35 U.S.C. 154(b) by 1207 days.

(21) Appl. No.: 12/809,143

(22) PCT Filed: Dec. 19, 2008

(86) PCT No.: PCT/FR2008/001795
§ 371 (c)(1),
(2), (4) Date: Jul. 28, 2010

(87) PCT Pub. No.: WO2009/103901
PCT Pub. Date: Aug. 27, 2009

(65) Prior Publication Data
US 2010/0311685 A1     Dec. 9, 2010

(30) Foreign Application Priority Data

Dec. 21, 2007  (FR) ..................... 07 09005

(51) Int. Cl.
| | | |
|---|---|---|
| *A61K 9/00* | (2006.01) | |
| *A61K 31/341* | (2006.01) | |
| *A61K 31/4155* | (2006.01) | |
| *A01N 47/02* | (2006.01) | |
| *A61K 31/415* | (2006.01) | |
| *A61K 47/10* | (2006.01) | |

(52) U.S. Cl.
CPC ............. *A61K 9/0017* (2013.01); *A01N 47/02* (2013.01); *A61K 31/341* (2013.01); *A61K 31/415* (2013.01); *A61K 31/4155* (2013.01); *A61K 47/10* (2013.01)

(58) Field of Classification Search
None
See application file for complete search history.

(56) References Cited

U.S. PATENT DOCUMENTS

| | | | | |
|---|---|---|---|---|
| 4,963,575 | A | * | 10/1990 | Buntain et al. ............... 514/359 |
| 8,486,374 | B2 | * | 7/2013 | Tamarkin et al. ............. 424/45 |
| 2004/0146557 | A1 | * | 7/2004 | Chern et al. .................. 424/468 |
| 2004/0198676 | A1 | * | 10/2004 | Soll et al. ...................... 514/28 |
| 2005/0191343 | A1 | * | 9/2005 | Liang .......................... 424/450 |
| 2005/0192319 | A1 | * | 9/2005 | Boeckh et al. ............... 514/341 |

FOREIGN PATENT DOCUMENTS

WO    WO 97/12521 A1    4/1997

OTHER PUBLICATIONS

Heukelbach et al. (Lancet, vol. 363, No. 9412, abstract; Mar. 2004).*
Lashmar, U. T. et al., *Topical Application of Penetration Enhancers to the Skin of Nude Mice: a Histopathological Study*, J. Pharm. Pharmacol., 41, (1989), pp. 118-122.
Summary of Product and Characteristics. Frontline Spot on Cat, Merial Animal Health Limited, (2007), pp. 1-7.
International Search Report for Application No. PCT/FR2008/001795 dated Sep. 28, 2009.

* cited by examiner

*Primary Examiner* — Jeffrey S Lundgren
*Assistant Examiner* — Meghan Finn
(74) *Attorney, Agent, or Firm* — Alston & Bird LLP

(57) ABSTRACT

The present invention relates to a liquid pharmaceutical composition containing an N-phenylpyrazole derivative as active ingredient and alpha-(tetrahydrofuranyl)-omega-hydroxy-poly(oxy-1,2-ethanediyl) as solvent for the treatment and/or prevention of infestations with fleas in domestic animals.

14 Claims, No Drawings

PHARMACEUTICAL COMPOSITION CONTAINING AN N-PHENYLPYRAZOLE DERIVATIVE AND GLYCOFUROL, USE FOR THE PREPARATION OF A TOPICAL VETERINARY MEDICAMENT FOR COMBATING FLEAS

FIELD OF THE INVENTION

The present invention relates to a liquid pharmaceutical composition containing an N-phenylpyrazole derivative as active ingredient and alpha-(tetrahydrofuranyl)-omega-hydroxypoly(oxy1,2ethanediyl) as solvent, and also to the use of such a composition for the preparation of an antiparasitic veterinary medicament for topical application, for the prevention and/or treatment of infestations with fleas in domestic animals, in particular in dogs and cats.

BACKGROUND OF THE INVENTION

Pets are often infested with one or more blood-feeding parasites such as dog or cat fleas, ticks or alternatively mange mites.

Fleas are wingless insects which have a laterally compressed body and highly developed legs suitable for jumping. They are blood-sucking ectoparasites of mammals or birds. The some 2000 species listed belong to the order Siphonaptera. Two species of fleas are commonly encountered in Europe; they are the cat flea (*Ctenocephalides felis*) and the dog flea (*Ctenocephalides canis*) which live in the fur of the animals. The cat flea, which is the most common, is capable of reproducing on both cats and dogs. It can also attack humans and other pets; however, the cat is the main animal responsible for infestation when cats and dogs live in the same environment.

Fleas have a complex life cycle with four distinct stages: egg, larva, pupa and adult. They mate in the first 8 to 48 hours following acquisition by the host, after their first blood meal. The females thus begin to lay eggs 24 to 48 hours after this first blood meal. The adult flea generally lays eggs on the animal. The eggs laid on the animal do not however remain there, and fall to the ground. Under optimum conditions, the female can lay more than 25 eggs a day. She will lay several hundred throughout her life. After a few days, a hairy white wormlike larva, approximately 1.5 mm long, is born. The larva feeds on organic debris, on larval remains and on dry blood defecated by the adults. The larval state lasts 1 to 3 weeks, if conditions are favorable (18° to 27° C. and 70% relative humidity). The larva then spins a cocoon and pupates. Normally, the pupa evolves in 1 to 2 weeks, but passage to the adult state can extend to 1 year, if conditions are unfavorable. The adult flea (small and black) emerges from the cocoon when it detects vibrations, heat, or a higher concentration of carbon dioxide, which occurs when a cat, a dog, etc., or a human(!) passes by. It then jumps onto the victim, immediately feeds on blood and rapidly grows, becoming a lighter reddish-brown color. The adult flea lives for 6 to 12 months. It can survive for up to 2 months without food.

Flea bites cause itching in both animals and humans. The flea saliva (secreted at each bite) can also, depending on individuals, lead to immediate or delayed allergic reactions. These reactions result in various skin lesions and itching. Two types of flea-related dermatosis are distinguished, namely pulicosis and flea allergy dermatitis. While in both cases the dermatosis results from a more or less substantial infestation with fleas, only in the second case is there an associated allergic phenomenon. Flea allergy dermatitis (FAD) is the most common cause of pruritas in dogs. In France, in adult dogs, it thus represents close to half of the pruritic dermatoses. Close to 80% of dogs which exhibit FAD also have atopic dermatitis, and, vice-versa, two atopic dogs out of three exhibit FAD. It is therefore probable that atopic dogs are predisposed to the development of a flea allergy and that infestation with the latter is a triggering factor for atopic dermatitis. This is proof of the need for a very intensive antiflea control in atopic dogs or dogs belonging to breeds at risk. Furthermore, FAD is probably the main cause of the reappearance of pruritis in desensitized atopic dogs.

Fleas of the *Ctenocephalides* genus are, moreover, intermediate hosts of *Dipylidium caninum*, which is a parasitic worm of the small intestine of dogs and cats. The carnivore becomes infested by swallowing the parasitized fleas. This infestation can cause anal pruritis, engorgement of the anal sacs, and also dermatitis of the perineal region. It is therefore sometimes recommended to worm animals regularly in addition to combating fleas.

Similarly, ticks (*Rhipicephalus* sp., *Ixodes* sp., *Dermacentor* sp., *Amblyomma* spa., etc.) can also cause the animal stress and be harmful to its health. They can also be harmful to humans. However, the most serious problem with ticks is that they are a vector for pathogenic agents that can concern animals just as much as humans. Among the major diseases that have to be avoided, mention may be made of boreliosis (Lyme disease caused by *Borelia burgdorferi*), babesiosis (piroplasmosis caused by *Babesia* sp.) and rickettsiosis. Ticks can also release toxins with paralyzing and inflammatory, and sometimes deadly, properties.

The mange mite (*Demodex* sp., *Sarcoptes* sp., *Otodectes* sp., etc.) is particularly difficult to combat since very few effective active materials exist. It requires frequent treatments.

Infestations with these various parasites, and most particularly flea infestations, therefore represent a considerable health problem for animals which are infested and make it necessary to be able to have suitable treatments. It is in particular advisable for the treatment to have not only an immediate effect (rapidity of action), but also an efficacy sustained over time (persistence) in order to avoid, on the one hand, repeat treatments and, on the other hand, any risk of infestation and/or reinfestation for a sustained period. The flea, in particular, must be eliminated before it reproduces and begins to lay eggs.

There are various insecticidal substances that are more or less active and more or less expensive. Resistance phenomena related to their use emerge, and this is in particular the case when carbamates, organophosphorus compounds and pyrethroids are used.

Moreover, patent applications EP 0 295 117 and EP 0 352 944 describe a large family of N—phenylpyrazoles which have a very broad spectrum of activity, including antiparasitic activities.

Although they are effective, N-phenylpyrazole derivatives, and in particular 5-amino-1-[2,6-dichloro-4-(trifluoromethyl)phenyl]-4-(trifluoromethylsulfinyl)-1H-pyrazole-3-carbonitrile (fipronil), are sometimes difficult to formulate since they do not always have sufficient solubility in the excipients conventionally used for preparing ready-to-use liquid antiparasitic compositions.

In fact, the products that are active against blood-sucking parasites, and in particular against fleas, can in particular be in the form of liquid compositions (pipettes) or "spot-on" solutions for the skin, that are applied very easily, in one go, topically, directly to the skin of the animal, generally between the shoulder blades.

However, in this type of composition, fipronil is often difficult to formulate and can produce crystallization phenomena. In order to overcome this problem, it has already been proposed, in particular in patent application EP 0 881 881, to formulate N-phenylpyrazole derivatives in a solvent medium in the presence of a crystallization inhibitor. The product Frontline® Spot-On Chat et Chien [Frontline® Spot-On for cats and dogs], sold in France by the company Merial SAS falls within this technology.

Such compositions, while they are very suitable for avoiding the problems of crystallization of these particular active ingredients, are not, however, always entirely satisfactory as regards the duration of protection that they confer on the animal. In the case of the product Frontline® Spot-On Chat et Chien in particular, the duration of protection against new flea infestations, stated by the manufacturer, is limited to 4 weeks in cats and 2 months in dogs. However, antiparasitic efficacy trials carried out according to the current standards do not make it possible to reproduce these sustained efficacy results, and the product does not therefore always have a completely satisfactory persistence.

SUMMARY

Therefore, in order to remedy all the problems encountered with the antiparasitic products currently available on the market and to provide a product for effectively preventing and treating infestations with fleas in domestic animals, both in cats and in dogs, the inventors have developed what forms the subject of the invention. They have in particular given themselves the aim of providing a product for the prevention and treatment of infestations with fleas in domestic animals which is easy to formulate and easy to administer, while at the same time having a rapid and more persistent action than the products currently available on the market.

Another objective of the invention is to provide such compositions which can be easily used irrespective of the animal species, the size of the animal or the nature of its coat.

Another objective of the invention is to have effective compositions which do not require the entire animal to be wetted.

These objectives are achieved by means of the antiparasitic pharmaceutical composition which is the subject of the present invention.

DETAILED DESCRIPTION

Unexpectedly, the antiparasitic pharmaceutical composition of the invention provides an effective and sustained activity in the treatment and protection of domestic animals in the form of a ready-to-use solution which is easy to use. It also makes it possible to formulate fipronil without any crystallization phenomenon being observed.

Thus, the subject of the present invention is a liquid pharmaceutical composition, characterized in that it contains:
- -5-amino-1-[2,6-dichloro-4-(trifluoromethyl)phenyl]-4-(trifluoromethylsulfinyl)-1H-pyrazole-3-carbonitrile (fipronil) as active ingredient, and
- alpha-(tetrahydrofuranyl)-omega-hydroxypoly(oxy-1,2-ethanediyl) as solvent.

Alpha-(tetrahydrofuranyl)-omega-hydroxypoly(oxy-1,2-ethanediyl), also called glycofurol, is a solvent that is well known in the pharmaceutical industry; it is, however, normally used as a solvent in pharmaceutical compositions to be administered by injection.

According to the invention, said pharmaceutical composition is in particular intended to be administered to cats or to dogs.

Within the pharmaceutical composition used in accordance with the invention, fipronil preferably represents from 1 to 20 g approximately per 100 ml of composition, and even more preferably from 5 to 15 g approximately per 100 ml of composition. It should be clearly understood, however, that these amounts are given by way of indication and that they can be modulated according to the needs of the formulation, in particular considering the effective doses according to the animal to be treated and to the weight of said animal.

The pharmaceutical composition used in accordance with the invention may also contain one or more excipients that can, for example, be chosen from surfactants, thickeners, dyes, fragrances and antioxidants, among which mention may, by way of nonlimiting example, be made of butylhydroxyanisol, butylhydroxytoluene, propyl gallate, ascorbyl palmitate and extracts of rosemary, and mixtures thereof.

When it (they) is (are) present, the antioxidant(s) preferably represent(s) from 0.005% to 2% by weight approximately, and even more preferably from 0.01% to 0.1% by weight approximately, relative to the total volume of the composition.

In addition to fipronil, the pharmaceutical composition may also comprise one or more additional antiparasitic active ingredients. By way of additional antiparasitic active ingredient, mention may in particular be made of acaricides such as amitraz or cymiazole, insect growth regulators, often referred to as IGRs, for fleas and ticks, such as pyriproxyfen and ethoxazole, endoparasiticides such as avermectins and derivatives thereof, for instance ivermectin, abamectin, doramectin and moxydectin, milbemycins, and also compounds that are active against sandflies and ectoparasites of domestic animals.

Such combinations of active agents may be useful with a view to broadening the spectrum of action of the composition in accordance with the present invention.

The pharmaceutical composition in accordance with the invention can easily be prepared by simply diluting the fipronil and, optionally, the additional antiparasitic active ingredient(s) in the glycofurol.

After it has been prepared, the pharmaceutical composition is preferably packaged in single-dose pipettes.

Another subject of the present application is the use of a liquid pharmaceutical composition as described above, for the preparation of an antiparasitic veterinary medicament for topical application, for the prevention (protection) and/or treatment of infestations with fleas in domestic animals, in particular in dogs or cats.

According to this use, said medicament is intended to be applied by direct application to the skin of the animal, at the level of the shoulder blades or on a dorsal line starting from the base of the tail and going up to the neck.

The amount of medicament to be administered can range from 0.3 to 1.5 ml approximately, preferably 0.5 ml approximately, in cats and from 0.3 to 6.0 ml approximately in dogs, depending on the weight of the animal under consideration and on the dosage.

The volume to be applied according to the invention should preferably correspond to a unit dose of fipronil ranging from 0.3 to 60 mg per kg of body weight, and even more preferably from 5 to 15 mg per kg of body weight.

Thus, according to a preferred embodiment of the invention, said medicament is intended to be administered at a unit dose of fipronil ranging from 0.3 to 60 mg per kg of body weight, and even more preferably from 5 to 15 mg per kg of body weight.

In addition to the above arrangements, the invention also comprises other arrangements which will emerge from the description which follows, which refers to an example of preparation of a pharmaceutical composition in accordance with the invention, and also to an example demonstrating the efficacy of said composition with respect to the treatment of fleas in dogs.

It should be clearly understood, however, that these examples are given only by way of illustration of the subject of the invention, of which they in no way constitute a limitation.

EXAMPLE 1

Study of the Efficacy of a Composition in Accordance with the Invention Against Fleas in Dogs In this example, a study which was intended to determine and compare the efficacy of two fipronil-based topical compositions was carried out:
 a composition A in accordance with the invention made up of fipronil and glycofurol;
 the product sold under the name Frontline® Top Spot by the company Mérial.

1) Materials and Methods
a) Type of Study
It is a randomized, blind, controlled study of efficacy carried out in parallel on three groups of six dogs.
b) Animals Used and Maintenance Conditions
The dogs used in this study were male or female mongrel dogs belonging to the *Canis familiaris* species, more than 6 months old, weighing between 6 kg and 25 kg. Before the beginning of the study, it was verified that all the dogs were in good health and that they were not infested with fleas. All the dogs were wormed and acclimatized to the living conditions for at least 7 days before the study was begun.

It was also verified that the dogs had received no topical treatment against fleas for 12 months preceding the beginning of the study.

During the acclimatization period and throughout the duration of the study, the dogs were kept inside a climatized room, each dog being confined in an individual pen having dimensions of 1.9 m×2.97 m, without litter and without any possible contact between the various dogs involved in the study. The identification number, the group number and the type of composition administered were noted outside each pen. The temperature of the room was kept at approximately 20° C.±4° C. The dogs were subjected to an alternating 12 hours of light and 12 hours of darkness.

The animals were fed once a day with commercial dry dog food sold under the trade name Ultradog Superwoof by the company Nola, a division of Foodcorp., according to the manufacturer's recommendations, and they had fresh drinking water ad libitum.
c) Compositions Tested
The following composition A in accordance with the invention was prepared:

| | |
|---|---|
| Fipronil | 10 g |
| Butylhydroxyanisole | 0.02 g |
| Butylhydroxytoluene | 0.01 g |
| Glycofurol q.s. | 100 ml |

This composition was compared with the product Frontline® Top Spot sold by the company Merial, containing 10% (g/100 ml) of fipronil and a mixture of excipients. It was used as provided by the manufacturer.
d) Treatments
 Group 1: Treatment with composition A in a proportion of 0.067 ml per kg of body weight,
 Group 2: Treatment with the product Frontline® Top Spot in a proportion of 0.067 ml per kg of body weight,
 Group 3: Negative control: no treatment.

The treatment was applied topically, between the shoulder blades of the dogs, in one go, at the beginning of the study (D=0).
e) Infestations with Fleas/Measurement of Treatment Efficacy 6 days before the beginning of the study (D=−6), all the dogs were infested with approximately 100 laboratory fleas, strain *Ctenocephalis felis*, of male or female gender. The fleas were then counted 5 days before the start of the treatment (D=−5). To do this, all the fleas present on an animal are harvested by combing the dog, and then counted after combing. The number of fleas is thus determined. After counting, and before administration of the treatment, the fleas are put back on the animal.

The number of fleas still alive 1 day after administration of the composition (D=1) was then counted.

The dogs were again infested with a known amount of fleas (approximately 100) 7 days (D=7), 14 days (D=14), 21 days (D=21), 35 days (D=35), 42 days (D=42), 49 days (D=49) and 56 days (D=56) after administration of the treatment.

A count of the fleas still alive was then performed 24 hours after each of these further infestations (D=8; D=15; D=22; D=36; D=43; D=50 and D=57).

At each count, the efficacy of the treatment was calculated according to the following equation:

$$\% \text{ efficacy} = 100 \times (NF_1C - NF_1T)/NF_1C$$

in which:
 $NF_1C$ is the geometric mean of the number of live fleas counted on the dogs of group 3 (control);
 $NF_1T$ is the geometric mean of the number of live fleas counted on the dogs of a group having received a treatment (group 1 or 2).

A treatment is said to be effective if the percentage efficacy is greater than or equal to 95%.
2) Results
The mean results obtained are given in table I below:

TABLE I

| Days | GROUP 1 (Composition A) | GROUP 2 (Frontline ® Top Spot) |
|---|---|---|
| D = 1 | 93.6 | 84.4 |
| D = 8 | 99.1 | 99.8 |
| D = 15 | 99.8 | 99.8 |
| D = 22 | 99.8 | 100.0 |
| D = 29 | 99.5 | 98.7 |
| D = 36 | 99.4 | 96.9 |
| D = 43 | 98.8 | 96.8 |
| D = 50 | 97.0 | 93.7 |
| D = 57 | 92.9 | 74.8 |

These results show that:
 composition A acts more rapidly than the product Frontline® Top Spot (comparison of % efficacy at D=1);
 composition A in accordance with the present invention remains effective for 7 weeks (D=50) against infestations with fleas in dogs;
 the product Frontline® Top Spot remains effective for 6 weeks (D=43) against infestations with fleas in dogs.

The rapidity of action and the better persistence of composition A in accordance with the present invention are thus clearly demonstrated.

The invention claimed is:

1. A liquid pharmaceutical composition comprising:
   5-amino-1-[2,6-dichloro-4-(trifluoromethyl)phenyl]-4-(trifluoromethylsulfinyl)-1H-pyrazole-3-carbonitrile as active ingredient, and
   a sole solvent, said sole solvent consisting of alpha-(tetrahydrofuranyl)-omega-hydroxypoly(oxy-1,2-ethanediyl).

2. The composition as claimed in claim 1, characterized in that the 5-amino-1-[2,6-dichloro-4-(trifluoromethyl)phenyl]-4-(trifluoromethylsulfinyl)-1H-pyrazole-3-carbonitrile represents from 1 to 20 g per 100 ml of composition.

3. The composition as claimed in claim 2, characterized in that the 5-amino-1-[2,6-dichloro-4-(trifluoromethyl)phenyl]-4-(trifluoromethylsulfinyl)-1H-pyrazole-3-carbonitrile represents from 5 to 15 g per 100 ml of composition.

4. The composition as claimed in claim 1, characterized in that it also contains one or more excipients chosen from surfactants, thickeners, dyes, fragrances and antioxidants.

5. The composition as claimed in claim 4, characterized in that the antioxidants are chosen from butylhydroxyanisole, butylhydroxytoluene, propyl gallate, ascorbyl palmitate and extracts of rosemary, and mixtures thereof.

6. The composition as claimed in claim 4, wherein the amount of antioxidant is from 0.005% to 2% by weight, relative to the total volume of the composition.

7. The composition as claimed in claim 1, characterized in that it comprises one or more additional antiparasitic active ingredients.

8. A method of preventing or treating fleas infestations an animal, the method comprising the step of applying to an animal a composition comprising 5-amino-1-[2,6-dichloro-4-(trifluoromethyl)phenyl]-4-(trifluoromethylsulfinyl)-1H-pyrazole-3-carbonitrile as an active ingredient, and a sole solvent said sole solvent consisting of alpha-(tetrahydrofuranyl)-omega-hydroxypoly(oxy-1,2-ethanediyl).

9. The method of claim 8, wherein the animal is a cat or a dog.

10. The method of claim 8, wherein the animal is a cat and said composition is administered in an amount ranging from about 0.3 to 1.5 ml.

11. The method of claim 8, wherein the animal is a dog and said composition is administered in an amount ranging from about 0.3 to 6.0 ml.

12. The method of claim 8, wherein the active ingredient is from administered at a unit dose ranging from 5 to 15 mg per kg of body weight.

13. The method of claim 8, wherein the 5-amino-1-[2,6-dichloro-4-(trifluoromethyl)phenyl]-4-(trifluoromethylsulfinyl)-1H-pyrazole-3-carbonitrile represents from 1 to 20 g per 100 ml of composition.

14. The method of claim 8, wherein the composition is in a form of a solution, and in which is characterized by the absence of crystallization of the 5-amino-1-[2,6-dichloro-4-(trifluoromethyl)phenyl]-4(trifluoromethylsulfinyl)-1H-pyrazole-3-carbonitrile.

* * * * *